United States Patent [19]

Hess

[11] Patent Number: 5,766,142
[45] Date of Patent: Jun. 16, 1998

US005766142A

[54] RESTING HAND ORTHOSIS WITH FINGER SEPARATORS

[75] Inventor: Clarence E. Hess, Safety Harbor, Fla.

[73] Assignee: Restorative Care of America Incorporated, Clearwater, Fla.

[21] Appl. No.: 795,673

[22] Filed: Feb. 6, 1997

[51] Int. Cl.[6] ......................................... A61F 5/00
[52] U.S. Cl. ........................ 602/22; 602/20; 128/879
[58] Field of Search .................. 602/20–22, 62, 602/64, 12; 128/878–880; 2/20, 21

[56] References Cited

U.S. PATENT DOCUMENTS

| | | | |
|---|---|---|---|
| 950,633 | 3/1910 | Eastman | 2/20 X |
| 1,797,057 | 3/1931 | Foulke | 602/21 |
| 2,178,619 | 10/1939 | Knuteson | 2/20 X |
| 3,703,894 | 11/1972 | Galloway et al. | 602/21 |
| 3,815,588 | 6/1974 | Klausner | 602/20 X |
| 4,558,694 | 12/1985 | Barber | 602/21 |
| 4,619,250 | 10/1986 | Hasegawa | 128/DIG. 20 X |
| 4,798,199 | 1/1989 | Hubbard et al. | 602/21 |
| 5,069,203 | 12/1991 | Anderson | 602/21 |
| 5,248,292 | 9/1993 | Holland | 602/6 |
| 5,413,120 | 5/1995 | Grant | 128/879 X |
| 5,419,756 | 5/1995 | McConnell | 602/21 X |
| 5,600,853 | 2/1997 | Yewer, Jr. | 2/20 X |
| 5,637,078 | 6/1997 | Varn | 602/6 X |

*Primary Examiner*—Richard J. Apley
*Assistant Examiner*—Denise Pothier
*Attorney, Agent, or Firm*—Zarley, McKee, Thomte, Voorhees, & Sease

[57] ABSTRACT

A hand orthosis has a base member supporting the palm and fingers of a patient. The base member has a cover which extends at least over the finger support area. A plurality of spaced parallel forwardly extending finger separators extend outwardly from said cover to form a plurality of finger channels therebetween. A flexible strap is secured to the base member and extends laterally across the separators and the channels. The cover and the separators are composed of a washable perspiration absorbing material.

6 Claims, 3 Drawing Sheets

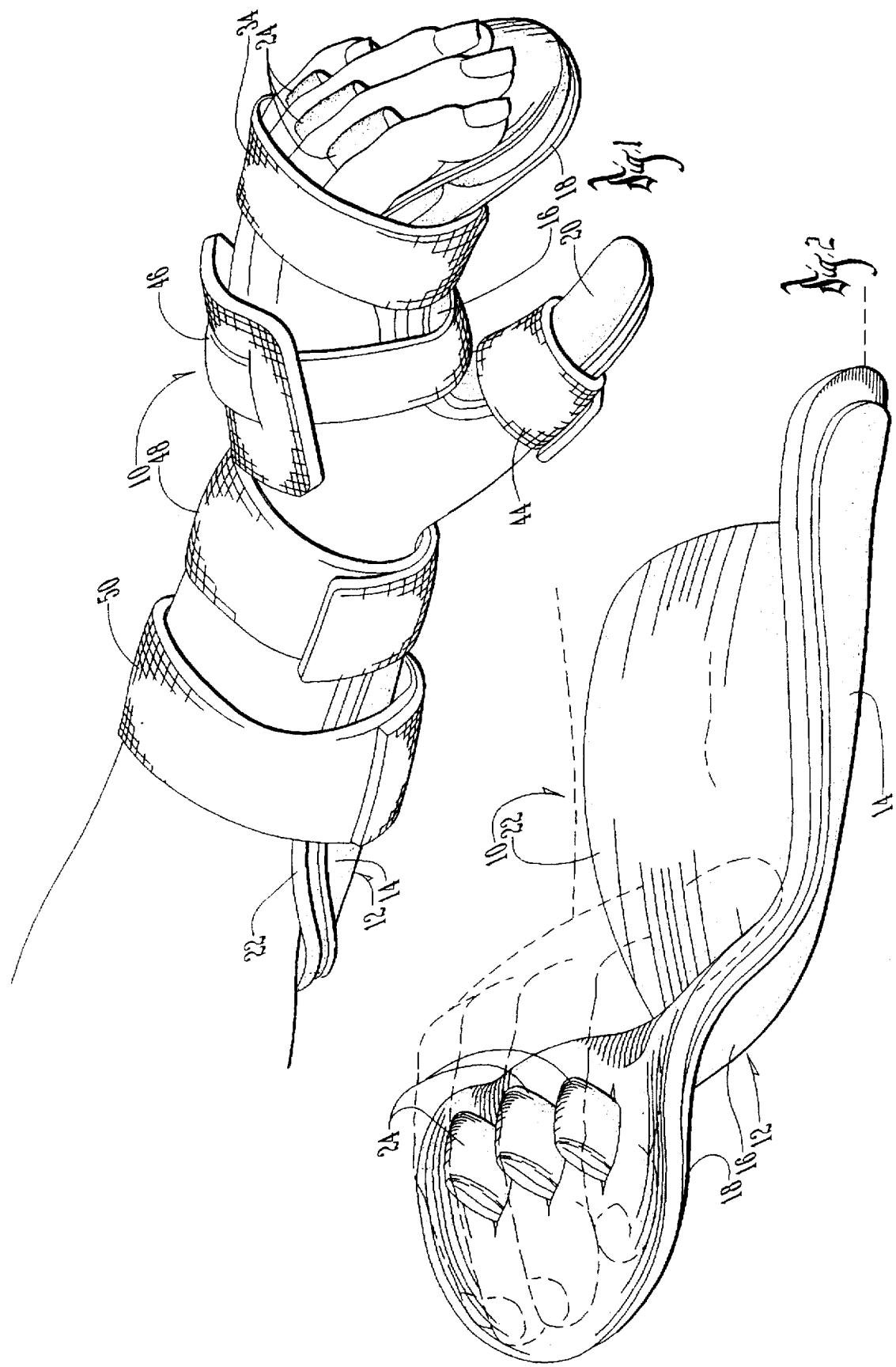

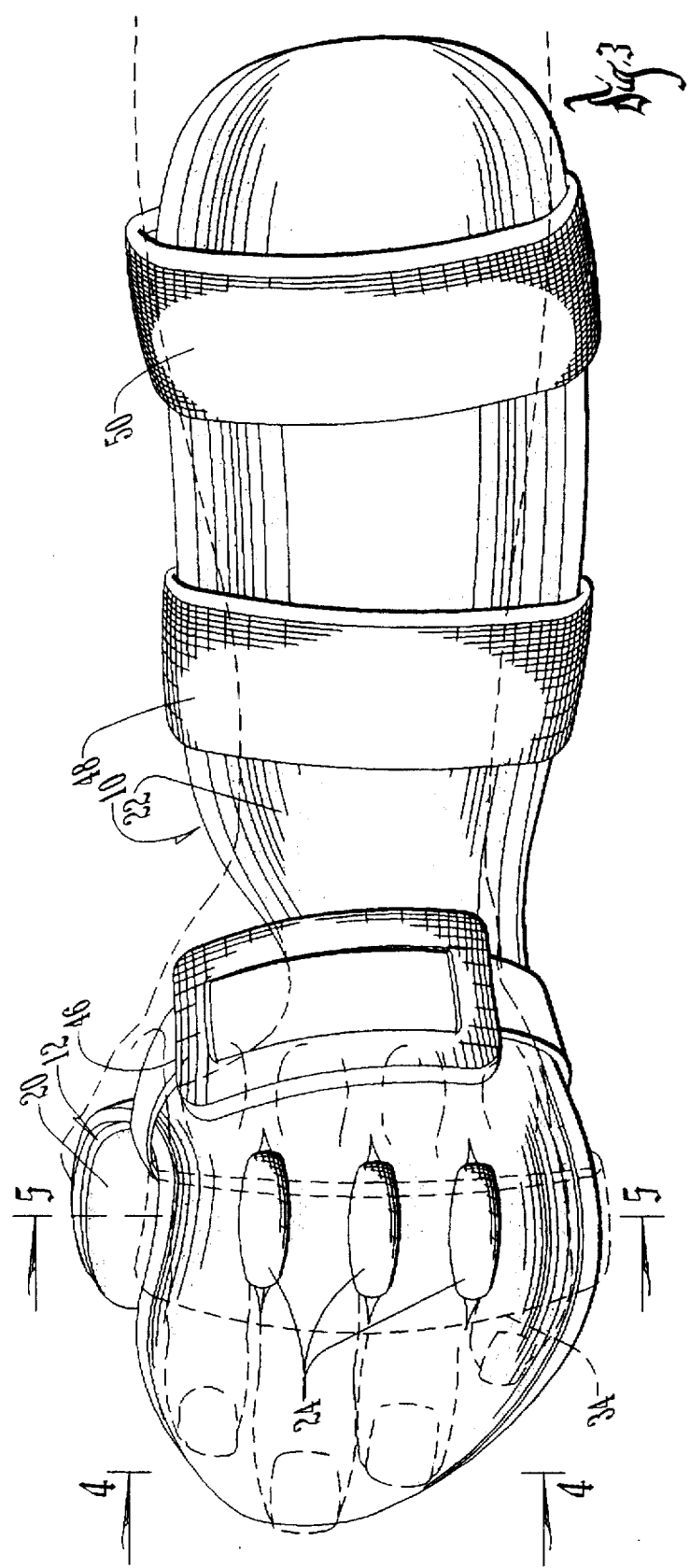

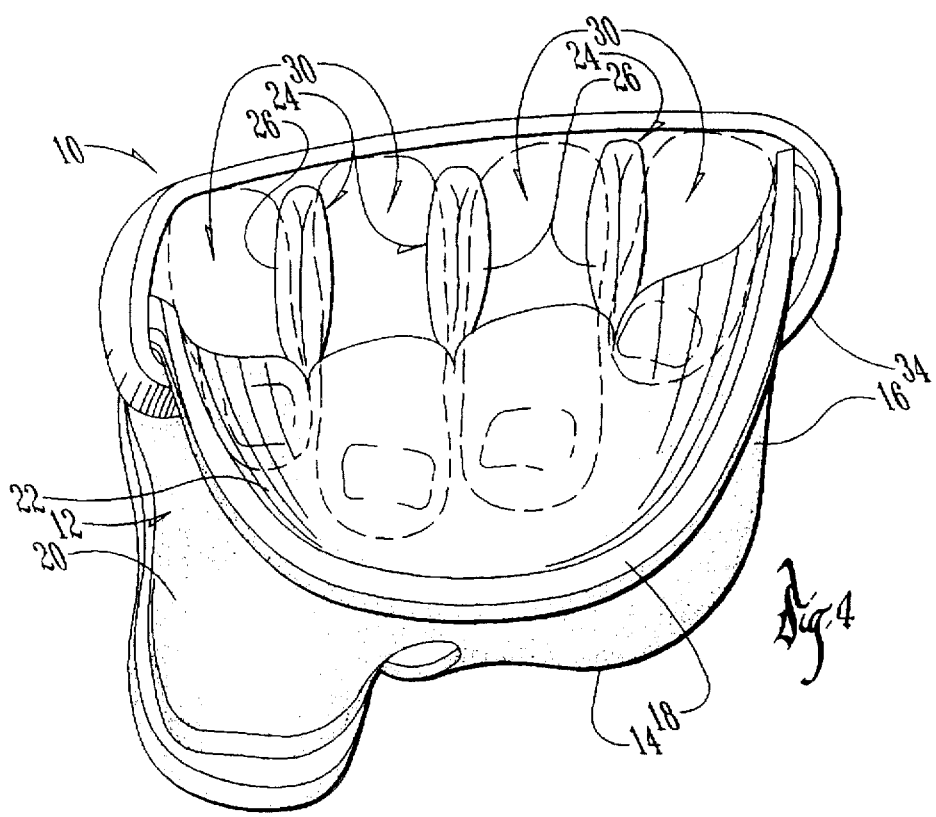
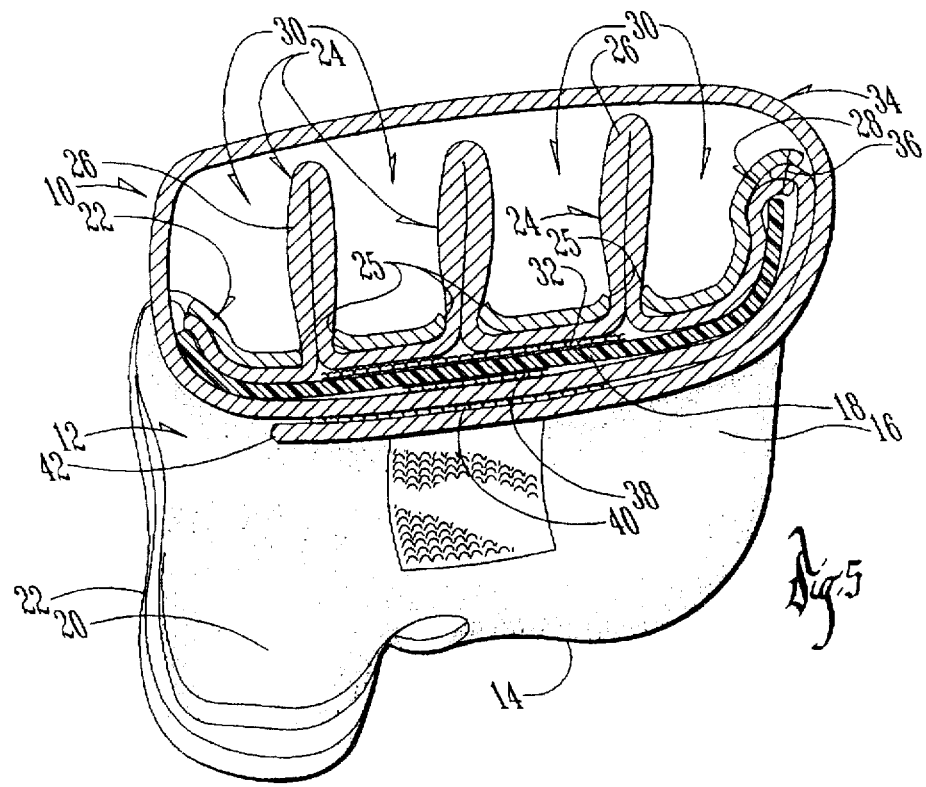

RESTING HAND ORTHOSIS WITH FINGER SEPARATORS

BACKGROUND OF THE INVENTION

Resting hand orthoses exist which provide a relatively stiff support member for the wrist, hand and fingers of a patient. The support members have a resilient cover to engage the patients' wrist, hand and fingers, and suitable straps are used to secure the device to the patients.

One of the problems of such existing orthoses is that they are not effective in promoting abduction, skin integrity between the fingers, and proper finger positioning. Further, they often require that the fingers be threaded through loops or slots which creates some of the foregoing problems, and makes the attachment of the orthoses to the patient more difficult.

It is therefore a principal object of the invention to provide a hand orthosis for patients which will promote abduction, skin integrity between the fingers, and proper finger positioning.

A further object of the invention is to provide a hand orthosis which would allow the patient's fingers to lie between spaced separators without requiring that the fingers be threaded through loops or slots.

A still further object of this invention is to provide a hand orthosis that can be easily laundered, and which will absorb perspiration.

These and other objects will be apparent to those skilled in the art.

SUMMARY OF THE INVENTION

The hand orthosis of this invention has a base member supporting the palm and fingers of a patient. The base member has a cover which extends at least over the finger support area. A plurality of spaced parallel forwardly extending finger separators extend outwardly from said cover to form a plurality of finger channels therebetween. A flexible strap is secured to the base member and extends laterally across the separators and the channels. The cover and the separators are composed of a washable perspiration absorbing material.

BRIEF DESCRIPTION OF THE DRAWINGS

FIG. 1 is a perspective view of the orthosis of this invention;

FIG. 2 is a perspective view of the orthosis with supporting straps removed;

FIG. 3 is a top plan view of FIG. 1 with the finger straps shown in dotted lines;

FIG. 4 is an end elevational view taken on line 4—4 of FIG. 3; and

FIG. 5 is a vertical view taken on line 5—5 of FIG. 3.

DESCRIPTION OF THE PREFERRED EMBODIMENT

The orthosis 10 of this invention has a stiff but deformable plastic splint 12 which serves as a base member for the orthosis. The splint 12 has a wrist portion 14, a hand or palm portion 16, a finger portion 18 (FIG. 2), and a thumb portion 20 (FIG. 1).

The splint 12 has a cover 22 extending over its interior surface. The cover 22 is secured to the splint 12 by a plurality of hook and loop attachment elements (not shown) and which do not comprise a part of this invention. These elements conventionally permit the cover 22 to be removed from the splint 12 as required. The foregoing structure is essentially conventional in a hand splint or orthosis.

The structure of this invention is directed to a plurality of finger separators 24 (see FIGS. 2 and 5) which extend through slits 25 in cover 22 and are comprised of a plurality of contiguous loops 26 which are formed out of an elongated strip 28 and are folded back against each other to extend through the slits 25 and to form the loops 26. (See FIG. 5). The strip 28 is comprised of perspiration absorbing material known as OrthoWick. This material promotes abduction and skin integrity between the fingers, and aids in proper finger positioning. As seen in FIG. 5, a plurality of open finger channels 30 are formed in-between the spaced separators 24. With reference to FIG. 5, a hook connector secured to splint 12 connects the mid portion of the strip 28 to the splint 12. A finger strap 34 has one of its ends sewn to the cover 22 at 36 (FIG. 5). A second hook attachment element 38 is located at the center of strip 28 and serves to detachably connect the strip to the exposed bottom surface of the splint 12. Similarly, a additional hook attachment element 40 is located at one end of strap 34 to be detachably secured to the center portion of the strap as it is folded over upon itself as shown in FIG. 5. The attachment element 40 is located adjacent the free end 42 of the strap.

A conventional thumb strap 44 extends around the patient's thumb and the thumb portion 20 of the splint 12 as best shown in FIG. 1. Similarly, a conventional hand strap 46 extends around the hand portion of splint 12. In like manner conventional wrist straps 48 and 50 extend around the splint 12 to further stabilize the orthosis 10 to the wrist of the patient. The straps 46, 48 and 50 are folded upon themselves and held in place by conventional hook attachment elements (not shown) which are conventional in the art. Also, straps 48 and 50 are secured to the cover 22 by sewing at one end thereof in the same manner that finger strap 34 was sewn to the cover at point 36. The structure of straps 46, 48 and 50 do not comprise a part of this invention.

It should be emphasized that the finger separators 24 are spaced with respect to each other to form the open finger channels 30 which are parallel to each other and which extend essentially vertically upwardly from the plane of the cover to which they are attached receiving and encompassing the bottom and sides of the patient's fingers. The open channels 30 permit the fingers of the patient to be moved downwardly and placed therebetween without the awkwardness and difficulty of moving the patient's fingers longitudinally through an open circular enclosed loop, for example.

The strip 28 is sewn to the cover 22 to avoid separation therefrom when the cover is removed from the splint 12 for laundering purposes.

As discussed above, this invention avoids the necessity of threading contracted or abducted fingers through loops or slots whereby the fingers are easily positioned in proper alignment on the orthosis.

The device of this invention offers a functional resting position following surgery or injury and provides finger and wrist stability. The orthosis 10 prevents or treats contractures and can be used under spastic conditions. The splint 12 is made of heat moldable Kydex plastic which can accommodate custom modification.

From the foregoing, it is seen that this invention will achieve at least its stated objectives.

What is claimed is:

1. A hand orthosis comprising, a base member for supporting the palm of a patient's hand, a finger support area adjacent to said base member and extending forwardly therefrom, a cover on said base member extending over said finger support area, a plurality of spaced parallel forwardly extending flexible finger separators on said cover extending outwardly therefrom to define a plurality of open finger channels therebetween so that a patient's fingers can be positioned in one each of said channels, said channels being defined by said cover and said finger separators, having a top portion that permits a patient's fingers to be moved downwardly into contact with said cover and having sufficient width and depth to receive and encompass the bottom and sides of the patient's fingers, and a flexible strap detachably secured to said base member and said cover and extends laterally across said separators and said finger channels to maintain the fingers of a patient within said channels.

2. The hand orthosis of claim 1 wherein second straps are secured to said base member to secure the hand of a patient to said hand orthosis.

3. The hand orthosis of claim 1 wherein said finger separators are comprised of a washable moisture absorbing material.

4. The device of claim 1 wherein said finger separators are comprised of an elongated strip which has a plurality of spaced closed loops formed therein to create said separators.

5. The device of claim 4 wherein said closed loops extend through spaced slits in said cover to define the width of said finger channels.

6. The device of claim 4 wherein said cover is removably mounted on said base member and said elongated strip is secured to said cover to prevent said finger separators from being detached from said cover when said cover is removed from said base member for laundering purposes.

* * * * *